United States Patent
Stam et al.

(10) Patent No.: US 11,071,270 B2
(45) Date of Patent: Jul. 27, 2021

(54) **PERICARP FREE *SPINACIA OLERACEA* SEEDS**

(71) Applicant: Bejo Zaden B.V., Warmenhuizen (NL)

(72) Inventors: Elisabeth Lucia Maria Stam, Heerhugowaard (NL); Jacob Van Dorp, Nieuwe Niedorp (NL); Nicolaas Anthonius Zutt, Avenhorn (NL); Albertus Johannes Maria Schrijver, Warmenhuizen (NL)

(73) Assignee: Bejo Zaden B.V., Warmenhuizen (NL)

( * ) Notice: Subject to any disclaimer, the term of this patent is extended or adjusted under 35 U.S.C. 154(b) by 191 days.

(21) Appl. No.: 16/305,287

(22) PCT Filed: May 30, 2016

(86) PCT No.: PCT/EP2016/062184
§ 371 (c)(1),
(2) Date: Nov. 28, 2018

(87) PCT Pub. No.: WO2017/207022
PCT Pub. Date: Dec. 7, 2017

(65) Prior Publication Data
US 2020/0253145 A1    Aug. 13, 2020

(51) Int. Cl.
*A01H 6/02* (2018.01)
*A01H 5/10* (2018.01)
*A01H 1/02* (2006.01)

(52) U.S. Cl.
CPC ............... *A01H 6/028* (2018.05); *A01H 1/02* (2013.01); *A01H 5/10* (2013.01)

(58) Field of Classification Search
None
See application file for complete search history.

(56) References Cited

U.S. PATENT DOCUMENTS

2005/0210744 A1    9/2005    Watanabe et al.

FOREIGN PATENT DOCUMENTS

| JP | 2283201 A | 11/1990 |
|---|---|---|
| JP | 2005270092 A | 10/2005 |
| WO | PCT/EP2016/06218 | * 12/2018 |

OTHER PUBLICATIONS

Hallavant & Ruas (2014) Veget Hist Archaeobot 23(2): 153-65.*
Tettelin et al. (2000) Science 287:1809-15.*
Arumuganathan et al. (1991) Genetic Resources 9:208-18.*
Yamamoto et al. (2014) Heredity 112:317-24.*
Irish et al. (2008) Phytopath 98(8):894-900.*
Hu et al., "Effects of the pericarp on imbibition, seed germination, and seedling establishment in seeds of Hedysarum scoparium Fisch. et Mey", Ecological Research, 2009, pp. 559-564, vol. 24.
Katzman et al., "Seed Enhancements to Improve Spinach Germination", HortScience, 2001, pp. 979-981, vol. 36, No. 5.
Suganuma et al., "Role of Pericarp in Reducing Spinach (*Spinacia oleracea* L.) Seed Germination at Supra-optimal Temperatures", Journal of the Japanese Society for Horticultural Science, 1984, pp. 38-44, vol. 53, No. 1.

* cited by examiner

*Primary Examiner* — Russell T Boggs
(74) *Attorney, Agent, or Firm* — The Webb Law Firm

(57) ABSTRACT

Provided herein are substantially pericarp free *Spinacia oleracea*, or spinach, seeds. Also provided herein are methods for producing substantially pericarp free *Spinacia oleracea*, or spinach, seeds and *Spinacia oleracea*, or spinach plant capable of producing substantially pericarp free seeds. Also provided herein are *Spinacia oleracea* seeds wherein the seeds are substantially free of pericarp and the seeds are obtainable by crossing a female *Spinacia oleracea* parent plant with a male *Spinacia oleracea* parent plant resulting in seed production by the female *Spinacia oleracea* parent plant, the female *Spinacia oleracea* parent homozygously comprises in its genome a recessive trait substantially preventing pericarp formation on seeds produced and harvesting *Spinacia oleracea* seeds substantially free of pericarp.

10 Claims, 4 Drawing Sheets

PERICARP FREE *SPINACIA OLERACEA* SEEDS

CROSS-REFERENCE TO RELATED APPLICATION

This application is the United States national phase of International Application No. PCT/EP2016/062184 filed May 30, 2016, the disclosure of which is hereby incorporated in its entirety by reference.

The present invention relates to substantially pericarp free *Spinacia oleracea*, or spinach, seeds. The present invention further relates to methods for producing substantially pericarp free *Spinacia oleracea*, or spinach, seeds and *Spinacia oleracea*, or spinach plants capable of producing substantially pericarp free seeds. The present substantially pericarp free *Spinacia oleracea*, or spinach, seeds provide, as compared to pericarp enclosed *Spinacia oleracea*, or spinach, seeds one or more of 1) a decreased volume and weight during transport, storage and handling, 2) a reduction of dormancy, 3) increased germination, 4) increased yield and 5) reduced pathogen pressure. The present invention further provides genetic sources in the form of a deposit which can be used for substantially pericarp free *Spinacia oleracea*, or spinach, seeds.

Spinach or *Spinacia oleracea* is an edible plant originating from Western and Central Asia. It belongs to the family Amaranthaceae. Formerly it was denoted as member of the Chenopodiaceae; this family however was merged in the Amaranthaceae around 2003, and now is the subfamily Chenopodioideae. It has been cultivated in Europe since around the year 1400.

Hybrids of spinach can readily be produced making use of plants which have a female flowering and plants which have a male flowering phase as pollinated plants. Before the female plants develop male flowers, all female flowers are fertilized by the male.

Three basic types of spinach are on the market:
A savoy type with dark green, curly and crinkly leaves (for the fresh market);
A flat, or smooth, leaf spinach with broad, smooth leaves that can be cleaned easily. This type is used for industry (canned or frozen spinach, as well as processed food and baby food;
Semi savoy is an intermediate type of spinach with a comparable texture as the savoy type but easy to clean as the smooth type of spinach. It is cultivated both for fresh market and industry.
an oriental type which is heat tolerant, has very little blistering of the leaves; long petioles, pointed leaves with several side lobes (or and as plant has an upright growth.

Breeding resulted in spinach plants which are rapid growing without premature flowering. Older varieties tend to have narrower leaves and have a stronger, somewhat bitter taste; newer varieties have broader leaves and a milder taste. Also, recent types have little tendency for bolting in warm conditions and therefore will not prematurely flower and produce seeds.

Regarding nutritional value, providing only a small amount of calories (only 23 for 100 grams of cooked spinach), spinach is a rich source of vitamins A, B2 (or folate), B6, C, E and K; magnesium, manganese, calcium, potassium, iron and dietary fibre.

*Spinacia oleracea* is an annual or biennial plant with smooth glossy leaves without trichomes. Initially leaves grow as a rosette; the stem grows erect and are mostly unbranched; the alternate leaves consist each of a petiole and a simple blade; this blade is triangular (or even arrow shaped) to ovular, sometimes with elongated lobes; with an entire or dentate margin and an acute apex. Sometimes red midveins are present in the leaves. In general plants are dioecious, also monoecious plants occur.

The male flowers are arranged in glomeruli forming interrupted terminal spike-like panicles. They each consist of 4-5 oblong perianth segments and 4-5 stamens. Female flowers are in glomeruli positioned in the leaf axils. Enclosed by two united bracteoles, without perianth, they consist of an ovary with 4-5 filiform stigmas. The chromosome base number is x=6, which is unusual for Chenopodioideae, more common in this family is x=9 or a multitude thereof. During seed set, bracteoles become enlarged and hardened and may have dentate margins, sometimes several flowers become united. The membranous pericarp adheres to the vertically orientated seed. The dark seed coat is spiny or smooth. The embryo is annular or ring shaped, surrounding the copious, grainy perisperm.

The pericarp is an outer layer of material surrounding the seed (with embryo, endosperm and seed coat); it is comprised of (from the outside to the inside) the exocarp; the mesocarp and the endocarp. With respect to seeds of *Spinacia oleracea*, the pericarp is forming a dry wall around the true seed. The presence of the pericarp around spinach seeds poses a number of practical problems in the art.

First, since the pericarp is relatively voluminous, the presence of the pericarp results in a vast increase of the volume of a seed lot. Both during transportation as well during storage, this is a serious problem. As a rule of thumb volume of pericarp hulled seeds is increased by a factor 2.5 and weight by a factor 1.7. Further, the presence of pericarp hampers gas exchange by and imbibition and germination of the seed; during germination the embryo has to break through this relatively strong layer of tissue. Further, the pericarp causes a strong dormancy effect in certain species; sometimes resulting in around 50% dormant seeds. The disadvantages of pericarp surrounding the spinach seeds can be summarized as follows:
Germination is hampered or delayed by the pericarp, either by mechanical hinderance or by causing dormancy;
Due to the structure of the pericarp, pathogens can be present in the pericarp and are difficult to remove by seed treatments;
The volume of the harvested seeds with pericarp is at least 2.5 times higher than that from pericarp-less seeds; weight is increased by a factor 1.7. This results in high costs for transport and storage.

In the past methods were developed to physically remove pericarp from seeds. Mechanical removal of the pericarp from *Hedysarum scoparium* resulted in improvement of the germination from 44% to 90% (Hu, X. W., Wang, Y. R. and Wu, Y. P. "*Effects of the pericarp on imbibition, seed germination, and seedling establishment in seeds of Hedysarum scoparium*"; Fisch. et Mey. Ecol. Res. 24: 559-564 (2009). In patent application JP1897972 (1990; "*Seed coat equipped seed and its production method*") a method is described to break a part of the seed coat by mechanical impact. First seeds are frozen to a temperature between −30 to −196° C., subsequently, at a temperature <=−7° C. seeds are mechanically treated to break the seed coat. In contrast to the prior art methods, studies performed to remove the pericarp from the seed by mechanical means were shown to result in a large portion of damaged seeds. Remaining seeds after these treatments had lower germination of the resulting seed lot, but germination of these remaining seeds was faster which also resulted in a higher yield per plant at harvest.

Another physical solution of the problem is found in patent application JP2005270092 (2005; "*Method for improving germination of hard seed by laser beam irradiation and germination improved seed*") disclosing a method of treating hard seeds of several species by laser beams to enhance germination. This treatment resulted in seeds which are perforated, enabling a better supply of oxygen and water to the embryo and/or an easier appearance of the embryo through the perforated pericarp or testa. The prior art methods require a lot of handling of the seeds and precise adjustment of equipment used and lead to seed losses due to damaging seeds.

It is an object of the present invention, amongst other objects, to at least partially, if not completely, solve the above problems of the prior art.

This object of the present invention, amongst other objects, is met providing seeds, methods and plants as outlined in the appended claims.

Specifically, according to a first aspect, this object of the present invention, amongst other objects, is met by providing *Spinacia oleracea* seeds wherein substantially all seeds are free of pericarp and wherein the seeds are obtainable by crossing a female *Spinacia oleracea* parent plant with a male *Spinacia oleracea* parent plant resulting in seed production by the female *Spinacia oleracea* parent plant. The female *Spinacia oleracea* parent homozygously comprises in its genome a recessive trait substantially preventing pericarp formation surrounding seeds produced.

According to the present invention, considering that pericarp is formed by the female parent and not by the progeny itself, substantially, or completely, seeds without pericarp can readily be obtained in any genetic background using a female parent line wherein the trait is functionally (homozygously recessive) present. Seed production with these female parent lines results essentially in 100% pericarp free F1 seeds. The spinach plants, grown from these seeds, are likely to bear wild type, pericarp covered seeds since the genetic trait is heterozygous in this generation.

Seed technological research on these pericarp free seeds revealed that they are less infected by pathogens and can easily be processed and treated by e.g. warm water for disinfection. Also the application of seed pelleting, encrusting or coating can be performed very well. In summary the advantages of the pericarp free seeds are:

The volume of the seeds to be transported and stored is reduced by 60%, the weight by 40%; this also can be envisaged as a more sustainable production method;

Reduction of dormancy Germination percentage is higher;

Germination is earlier resulting in a more uniform crop (see for example appended FIG. 2);

In a given growing period yield of the crop is higher (see for example appended FIG. 3);

Less risk of contaminating pathogens on the seed (see for example appended FIG. 4);

The absence of (at least in part) of seed borne pathogens results in healthier seeds and a possible reduction in the application of fungicides;

Pelleting, encrusting or coating of the seeds can be performed very well because of the smaller size and more regular shape;

These techniques also open up the possibility of special seed treatments as:

Addition of fungicides, insecticides (uniform distribution, less use);

Addition of benificials (advantageous microbes; biological control, micronutrients);

Priming of the pericarp free seeds is easier performed than priming of conventional spinach seeds and results in a more uniform product;

Addition of identification system like a certain colour (e.g. identifying organic seeds), microdots, synthetic DNA or fluorescent dyes is feasible.

According to a preferred aspect of the present invention, the present *Spinacia oleracea* seeds are hybrid seeds obtained by crossing the female *Spinacia oleracea* parent plant carrying the pericarp free trait with a male *Spinacia oleracea* plant being a different variety than said female *Spinacia oleracea* parent plant thereby readily producing hybrid seeds.

According to another preferred aspect of the present invention, the present *Spinacia oleracea* seeds can be grown into *Spinacia oleracea* plants being sterile, preferably male sterile.

According to an especially preferred embodiment, the present pericarp less trait, or the recessive trait substantially preventing pericarp formation, is obtainable, obtained or is from a *Spinacia oleracea* plant deposited at NCIMB under deposit number NCIMB 42555 on Feb. 25, 2016 (NCIMB Limited; Ferguson Building; Craibstone Estate; Bucksburn Aberdeen; Scotland, AB21 9YA, United Kingdom.) It is noted that the present trait is heterozygous present in the deposit and thus the deposit itself produces normal seeds (seeds surrounded by pericarp). Using well known Mendelian inheritance, the present trait can be readily obtained in a homozygous recessive form. Spinach plants carrying the homozygous recessive form of the present trait can be readily identified by their pericarp free seeds.

According to another aspect, the present invention relates to methods for producing *Spinacia oleracea* seeds free of pericarp, the methods comprise the step of:

crossing a female *Spinacia oleracea* parent plant with a male *Spinacia oleracea* parent plant resulting in seed production by the female *Spinacia oleracea* parent plant, the female *Spinacia oleracea* parent homozygously comprises in its genome a recessive trait substantially preventing pericarp formation on said produced seeds; and harvesting, isolating or collecting *Spinacia oleracea* seeds substantially free of pericarp.

According to a preferred embodiment of the present method, the female *Spinacia oleracea* parent plant is crossed with a male *Spinacia oleracea* plant being a different variety than said female *Spinacia oleracea* parent plant thereby producing hybrid *Spinacia oleracea* seeds, preferably sterile hybrid *Spinacia oleracea* seeds, more preferably male sterile hybrid *Spinacia oleracea* seeds.

According to an especially preferred embodiment of the present method, the present substantially preventing pericarp formation trait is obtainable, obtained, or is from a *Spinacia oleracea* plant deposited at NCIMB under deposit number NCIMB 42555 on Feb. 25, 2016.

According to yet another aspect, the present invention relates to *Spinacia oleracea* plants capable of producing seeds substantially free of pericarp wherein the *Spinacia oleracea* plant homozygously comprises in its genome a recessive trait substantially preventing pericarp formation on produced seeds. The present plants are preferably male sterile female plants.

According to an especially preferred embodiment, the present *Spinacia oleracea* plants comprise a recessive trait substantially preventing pericarp formation obtainable, obtained or being from a *Spinacia oleracea* plant deposited at NCIMB under deposit number NCIMB 42555 on Feb. 25, 2016.

According to still another aspect, the present invention relates to the use of a recessive trait capable of substantially preventing pericarp formation on seeds produced wherein the trait substantially preventing pericarp formation is obtainable, obtained, or is from a *Spinacia oleracea* plant deposited at NCIMB under deposit number NCIMB 42555 on Feb. 25, 2016 for the production of substantially pericarp free *Spinacia oleracea* seeds.

BRIEF DESCRIPTION OF THE DRAWINGS

The present invention will be further detailed in the example below. In the example, reference is made to figures wherein.

DESCRIPTION OF THE INVENTION

Example

Figure 1:
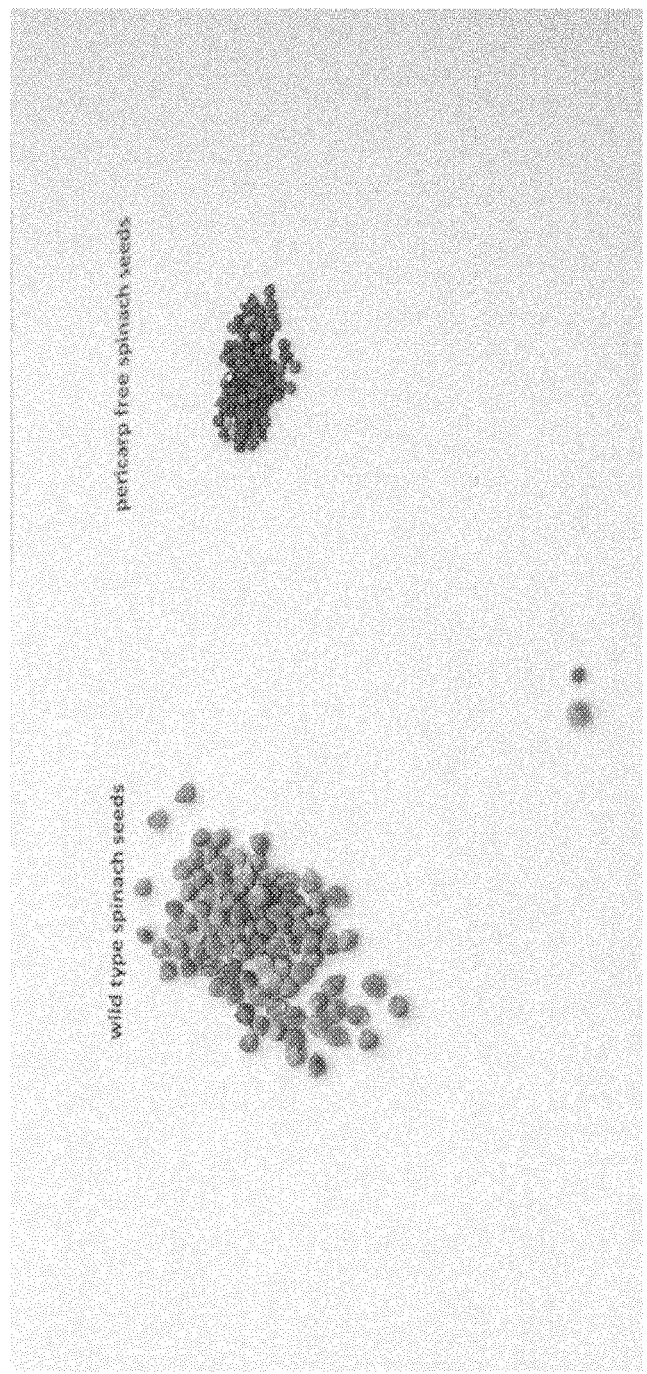
FIG. 1: shows of comparative photograph of the present seeds without pericarp (right) and seeds with pericarp.
Figure 2:
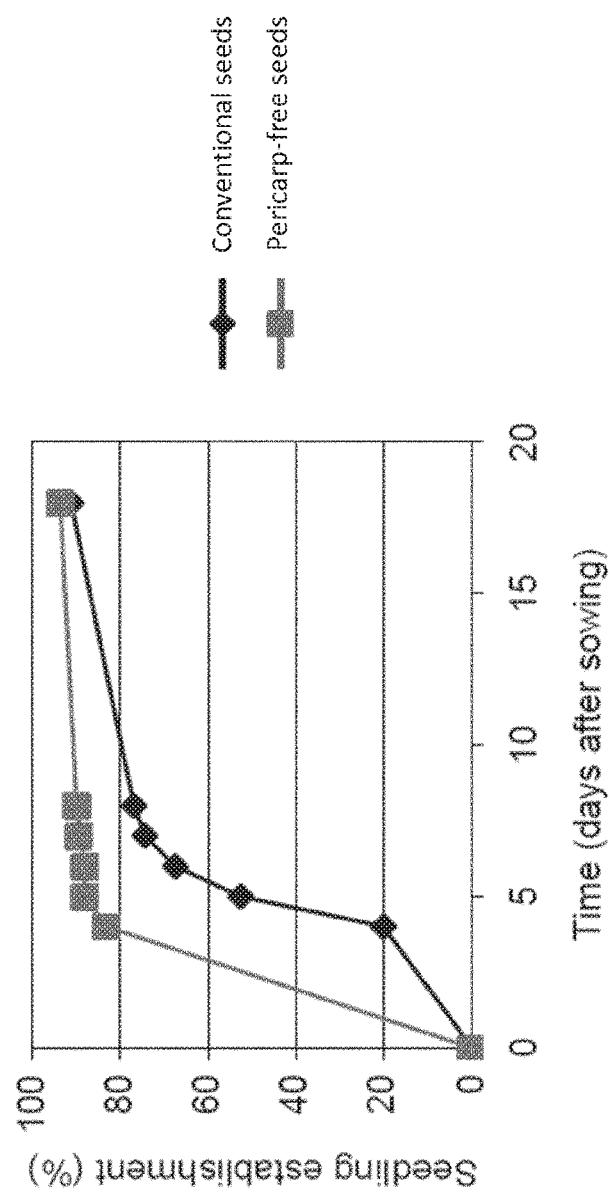
FIG. 2: depicts the time of appearance of seedlings after sowing conventional pericarp containing seeds and the present seeds without pericarp.
Figure 3:
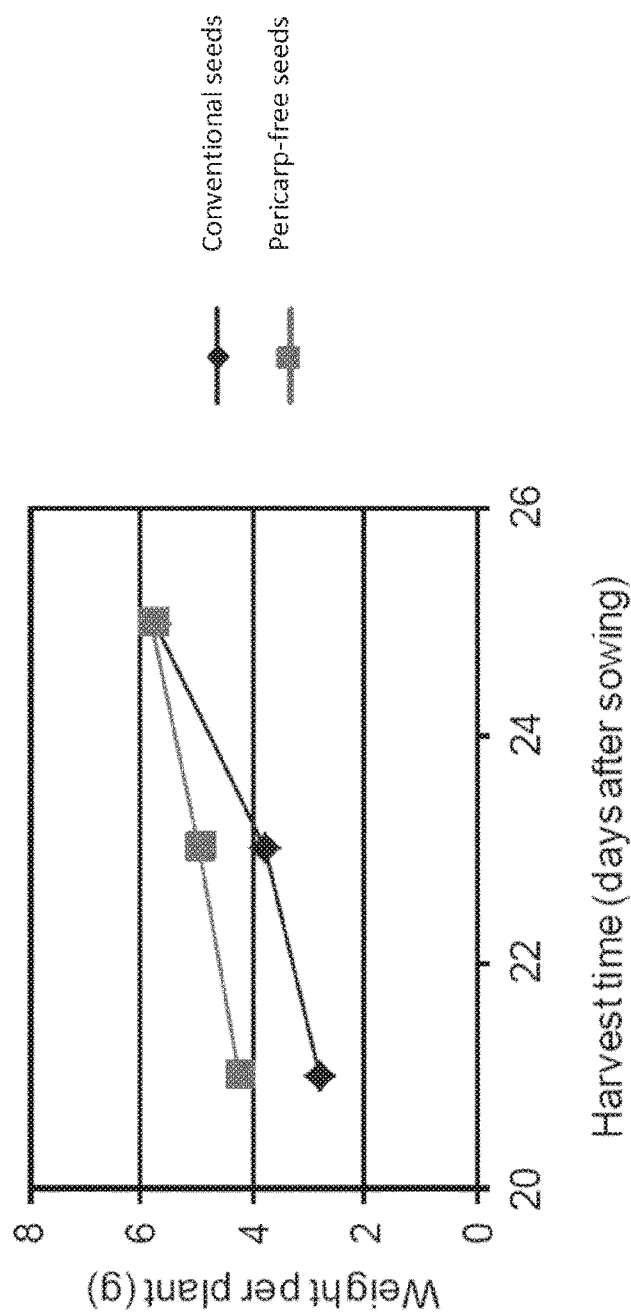
FIG. 3: depicts the weight per plant at different times after sowing of conventional pericarp containing seeds and the present seeds without pericarp.
Figure 4:
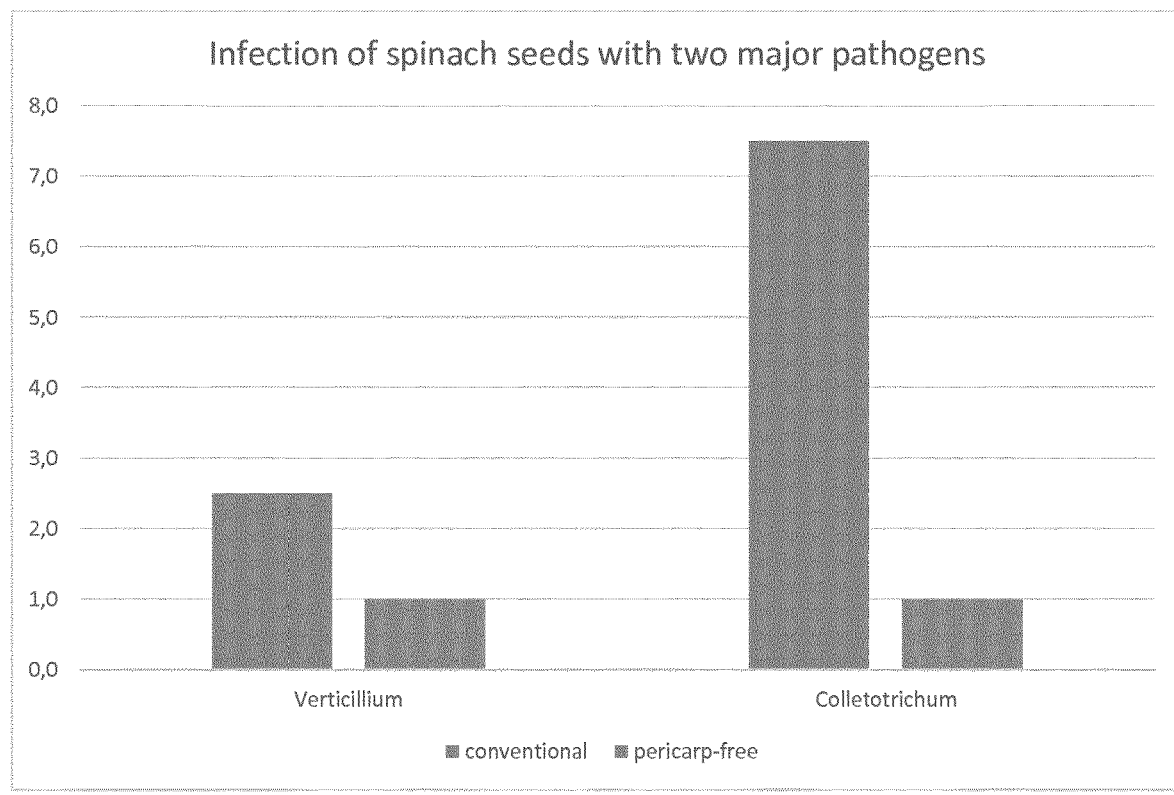
FIG. 4: shows the occurrence of pathogens using conventional pericarp containing seeds and the present seeds without pericarp.

Female *Spinacia oleracea* parent lines homozygously carrying the present trait were crossed with several male *Spinacia oleracea* parent lines with a different genetic backgrounds not carrying the present trait. Subsequently, substantially 100% seeds without pericarp were produced and collected. The collected seeds were subjected to standard viability, yield and disease tests. The results thereof are summarised in FIGS. 1 to 4.

As can be clearly seen in FIGS. 1 to 4, as compared to traditional Spinach seeds, weight/volume (FIG. 1); viability (FIG. 2); yield (FIG. 3) and disease resistance (FIG. 4) were significantly improved in the present seeds.

With respect to the physical properties of the present seeds (FIG. 1), weight of 1000 seeds (TGW, thousand grain weight) of both conventional as pericarp free seeds was determined. The average TGW of pericarp free seeds is 6.1-8.3 gram; of conventional seeds 11.1-12.5 gram. Another parameter determined is the average diameter of seeds; two different lots of pericarp free seeds and related conventional seeds were used to determine the diameter. In one fraction of seeds the conventional seeds had a diameter of 3 mm and pericarp free seeds of 2.6 mm; in a second seed lot the average diameter was 4.4 and 3.0 mm respectively. This means that the diameter of pericarp free seeds is 25-30% smaller than the diameter of conventional seeds.

Deposit Information

A deposit of a representative sample of a pericarp free spinach 1520124NZ was made on Feb. 25, 2016 at NCIMB Limited; Ferguson Building; Craibstone Estate; Bucksburn Aberdeen; Scotland, AB21 9YA, United Kingdom and was registered as NCIMB 42555.

Definitions

Coating:
A relatively thin layer of polymer is supplied to the seed; to this polymer fungicides or insecticides can be added to protect the seed against soil borne pathogens and insect damage. Additionally, a dye can be added, giving the opportunity to check for correct drilling of the seeds. Alternatively, also other beneficial compounds can be added as micronutrients or beneficials micro-organisms promoting the growth of the young seedlings.

Encrusting:
By encrusting the seeds not only are covered with a polymer with or without extra substances as described above but also the seeds are provided with a smooth surface. This makes drilling easier and the added weight enables a more precise direct drilling of seeds treated this way Pelleting:
With pelleting the seeds are covered with more material, e.g. polymer bound clay, to produce a regularly shaped, round pellet. This pellet, besides eventually having the protecting substances described above, can be constructed in such a way that it will melt or split after water uptake.

Priming:
Priming or pre-germination is a treatment were seeds are given enough moisture to have a onset of growth of the embryo inside the seed. This results in a faster emergence of the seedling, a higher emergence rate and better growth. It is believed that this head-start results in a good root system going down the soil early and faster growth.

Dormancy:
Dormancy prevents the germination of a seed for a certain period of time; normally dormancy prevents germination under unfavourable conditions but this delay can eventually be for a period of several months or even years.

Pericarp Free or Substantially Pericarp Free:
Pericarp free in the context of this application means that practically no pericarp is surrounding the true seed; however some minor remains of the pericarp may eventually be present.

The invention claimed is:

1. A *Spinacia oleracea* seed deposited under NCIMB Accession No. 42555, wherein said seed heterozygously comprises in its genome a recessive trait substantially preventing pericarp formation in a female *Spinacia oleracea* plant.

2. A method for producing a female *Spinacia oleracea* plant, the method comprises the steps of:
producing a first *Spinacia oleracea* parent plant from a *Spinacia oleracea* seed deposited under NCIMB Accession No. 42555, wherein said seed heterozygously comprises in its genome a recessive trait substantially preventing pericarp formation;
crossing said first *Spinacia oleracea* parent plant with a second *Spinacia oleracea* parent plant, wherein said second *Spinacia oleracea* parent plant comprises in its genome the recessive trait substantially preventing pericarp formation;
harvesting *Spinacia oleracea* seeds; and
selecting for said female *Spinacia oleracea* plant, wherein said female *Spinacia oleracea* plant produces a seed substantially free of pericarp.

3. The method according to claim 2, wherein said second *Spinacia oleracea* parent plant is a different variety than said first *Spinacia oleracea* parent plant, thereby producing a hybrid *Spinacia oleracea* seed.

4. An F1 female *Spinacia oleracea* plant grown from the method of claim 2, wherein said female *Spinacia oleracea* plant homozygously comprises in its genome the recessive trait that substantially prevents pericarp formation on seed produced from the female *Spinacia oleracea* plant.

5. The method of claim 3, wherein the *Spinacia oleracea* seed that is produced is a sterile hybrid seed.

6. The method of claim 3, wherein the *Spinacia oleracea* seed that is produced is a male sterile hybrid seed.

7. A method of generating a *Spinacia oleracea* seed that is substantially free of pericarp comprising, fertilizing said female *Spinacia oleracea* plant of claim 4 with a male *Spinacia oleracea* plant.

8. The method of claim 7, wherein the male *Spinacia oleracea* plant is a different variety than said female *Spinacia oleracea* parent plant, thereby producing hybrid *Spinacia oleracea* seed.

9. The method of claim 8, wherein said *Spinacia oleracea* seed that is produced is a sterile hybrid seed.

10. The method of claim 8, wherein said *Spinacia oleracea* seed that is produced is a male sterile hybrid seed.

* * * * *